(12) United States Patent
Yasuda et al.

(10) Patent No.: US 9,198,682 B2
(45) Date of Patent: Dec. 1, 2015

(54) ENDOSCOPE TREATMENT TOOL

(71) Applicants: OLYMPUS CORPORATION, Tokyo (JP); GIFU UNIVERSITY, Gifu-shi, Gifu (JP)

(72) Inventors: Ichiro Yasuda, Gifu (JP); Tsukasa Kobayashi, Tokyo (JP); Yutaka Yanuma, Tokyo (JP)

(73) Assignees: OLYMPUS CORPORATION, Tokyo (JP); GIFU UNIVERSITY, Gifu (JP)

( * ) Notice: Subject to any disclaimer, the term of this patent is extended or adjusted under 35 U.S.C. 154(b) by 0 days.

(21) Appl. No.: 13/910,677

(22) Filed: Jun. 5, 2013

(65) Prior Publication Data

US 2014/0012283 A1   Jan. 9, 2014

Related U.S. Application Data

(63) Continuation of application No. PCT/JP2012/059899, filed on Apr. 11, 2012.

(60) Provisional application No. 61/474,833, filed on Apr. 13, 2011.

(51) Int. Cl.
*A61B 17/221* (2006.01)
*A61B 17/00* (2006.01)

(52) U.S. Cl.
CPC ....... *A61B 17/221* (2013.01); *A61B 2017/0034* (2013.01); *A61B 2017/2212* (2013.01)

(58) Field of Classification Search
CPC ................. A61B 17/221; A61B 17/22; A61B 17/32056; A61B 17/26; A61B 17/0485; A61B 2017/2212
USPC ................................. 606/113, 127, 128, 200
See application file for complete search history.

(56) References Cited

U.S. PATENT DOCUMENTS 6,187,017 B1 *   2/2001   Gregory, Jr. ................... 606/127
7,004,954 B1     2/2006   Voss et al.
(Continued)

FOREIGN PATENT DOCUMENTS

CN          1308508 A      8/2001
JP          A-10-127648    5/1998
(Continued)

OTHER PUBLICATIONS

Oct. 24, 2013 Search Report issued in European Patent Application No. 12771556.3.
(Continued)

*Primary Examiner* — Jonathan W Miles
*Assistant Examiner* — Todd J Scherbel
(74) *Attorney, Agent, or Firm* — Oliff PLC

(57) ABSTRACT

An endoscope treatment tool includes a flexible sheath, a manipulation wire, and a basket portion constituted by a locking portion and a plurality of elastic wires. A maximum outside diameter portion of the basket portion is at a position closer to the locking portion than an intermediate position between a proximal end of the basket portion and the locking portion. The plurality of elastic wires is formed in a shape of a helix, and a winding pitch of the plurality of elastic wires becomes gradually smaller in a direction from a proximal side to the distal side of the manipulation wire. When a proximal side of the basket portion is reduced, an outside diameter of the maximum outside diameter portion is maintained at substantially a same size as the outside diameter before the proximal side of the basket portion is reduced.

8 Claims, 16 Drawing Sheets

(56) References Cited

U.S. PATENT DOCUMENTS

| | | | |
|---|---|---|---|
| 7,101,379 B2 * | 9/2006 | Gregory et al. | 606/127 |
| 8,377,092 B2 * | 2/2013 | Magnuson | 606/200 |
| 2003/0009191 A1 * | 1/2003 | Wensel et al. | 606/200 |
| 2003/0088254 A1 | 5/2003 | Gregory, Jr. et al. | |
| 2003/0153944 A1 | 8/2003 | Phung et al. | |
| 2006/0129166 A1 | 6/2006 | Lavelle | |
| 2007/0066991 A1 * | 3/2007 | Magnuson | 606/200 |

FOREIGN PATENT DOCUMENTS

| | | |
|---|---|---|
| JP | B2-3075355 | 8/2000 |
| JP | A-2003-33359 | 2/2003 |
| JP | A-2004-135945 | 5/2004 |
| JP | A-2005-21195 | 1/2005 |
| WO | 99/56801 A2 | 11/1999 |
| WO | WO 03/002006 | 1/2003 |

OTHER PUBLICATIONS

May 29, 2012 International Search Report issued in International Patent Application No. PCT/JP2012/059899 (with translation).

Dec. 31, 2014 Office Action issued in Chinese Patent Application No. 201280005159.1.

* cited by examiner

ENDOSCOPE TREATMENT TOOL

This application is a continuation application based on a PCT Patent Application No. PCT/JP2012/059899, filed on Apr. 11, 2012, whose priority is claimed on U.S. Provisional Patent Application No. 61/474,833, filed on Apr. 13, 2011. The contents of both the PCT Patent Application and the United States Provisional Patent Application are incorporated herein by reference.

BACKGROUND OF THE INVENTION

1. Field of the Invention

The present invention relates to an endoscope treatment tool.

2. Description of Related Art

In the related art, an endoscope treatment tool is known which is endoscopically inserted into the inside of a body and which grips foreign matter, such as a calculus generated inside the body, such as a biliary tract. For example, Japanese Patent Publication No. 3075355 discloses a cage-shaped basket composed of a plurality of elastic wires having folds. The basket described in Japanese Patent Publication No. 3075355 can snare a calculus therein from gaps in a plurality of elastic wires, and hook the calculus with the elastic wires, thereby gripping the calculus.

Additionally, Japanese Unexamined Patent Application, First Publication No. 2005-21195 discloses basket-type gripping forceps as another example of the endoscope treatment tool which grips a calculus. Japanese Unexamined Patent Application, First Publication No. 2005-21195 describes that a cage-shaped portion which receives a calculus therein is constituted by a plurality of elastic wires which is bent in a curved shape or a helical shape.

SUMMARY OF THE INVENTION

According to a first aspect of the present invention, an endoscope treatment tool includes: a flexible sheath; a manipulation wire inserted through the flexible sheath so as to freely advance and retract; and a basket portion which is connected to a distal side of the manipulation wire, is constituted by a locking portion provided at a distal end of the basket portion, and a plurality of elastic wires integrated by the locking portion, and opens and closes in a radial direction orthogonal to a central axis of the manipulation wire. A maximum outside diameter portion of the basket portion is at a position closer to the locking portion than an intermediate position between a proximal end of the basket portion and the locking portion in a direction of the central axis. The plurality of elastic wires is formed in a shape of a helix in which each of the plurality of elastic wires is wound in a same direction over an entire length of the plurality of elastic wires, and a winding pitch of the plurality of elastic wires becomes gradually smaller in a direction from a proximal side of the manipulation wire to the distal side of the manipulation wire. A tangential line of each of the plurality of elastic wires in the maximum outside diameter portion is inclined at an angle of 45° or less with respect to a plane orthogonal to the central axis without an external force applied to the basket portion, and thereby, when a proximal side of the basket portion is reduced, the maximum outside diameter portion is pushed outward in the radial direction by a first amount which is substantially a same as a second amount by which the proximal side of the basket portion is reduced inward in the radial direction, and an outside diameter of the maximum outside diameter portion is maintained at substantially a same size as the outside diameter before the proximal side of the basket portion is reduced.

According to a second aspect of the present invention, in the endoscope treatment tool according to the first aspect, the basket portion may include a support member coupled to the locking portion which is at least partially inserted into the flexible sheath.

According to a third aspect of the present invention, in the endoscope treatment tool according to the second aspect, the support member may be arranged at a position shifted from a centerline of the plurality of elastic wires integrated by the locking portion.

According to a fourth aspect of the present invention, the endoscope treatment tool according to the second aspect may further include a coupling portion further extending to a distal side of the basket portion from the locking portion. The support member may be fixed to the coupling portion.

According to a fifth aspect of the present invention, in the endoscope treatment tool according to the first aspect, the elastic wires may be made of a nickel titanium alloy.

According to a sixth aspect of the present invention, in the endoscope treatment tool according to the first aspect, the plurality of elastic wires may be wound counterclockwise, as seen from a proximal end of the manipulation wire toward a distal end of the manipulation wire.

DETAILED DESCRIPTION OF THE INVENTION

An endoscope treatment tool 1 according to a first embodiment of the present invention is described with reference to FIGS. 1 to 15.

First, the configuration of the endoscope treatment tool 1 is described.

Figure 1:
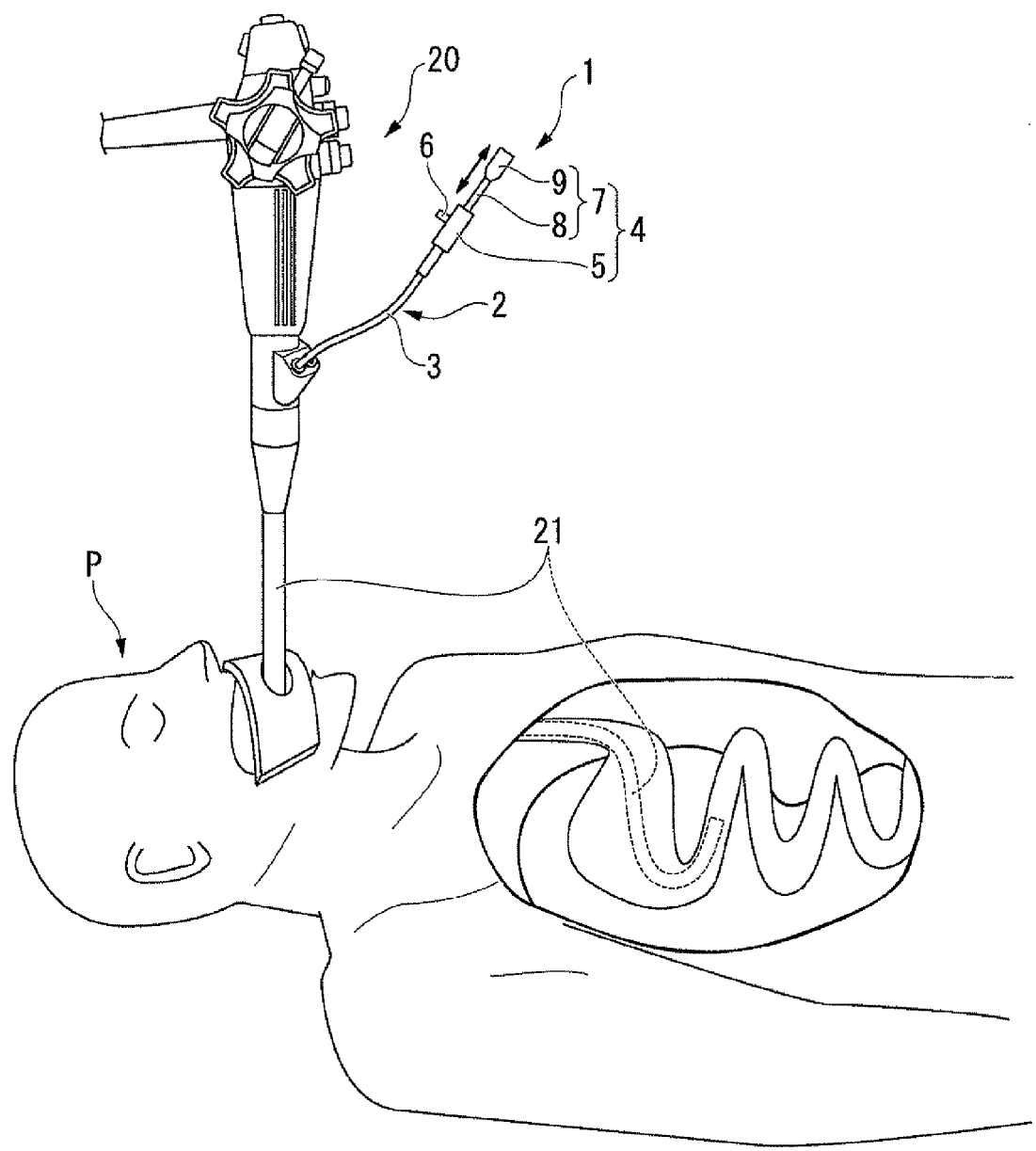
FIG. 1 is a view showing a state where an endoscope treatment tool according to a first embodiment of the present invention and an endoscope apparatus used along with the endoscope treatment tool are combined together.
Figure 2:
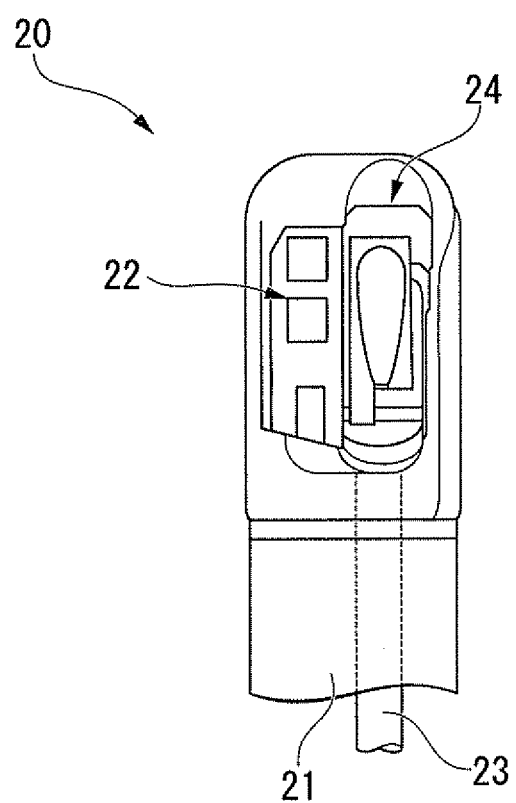
FIG. 2 is an enlarged view showing a part of the endoscope apparatus in an enlarged manner.

FIG. 1 is a view showing a state where the endoscope treatment tool 1 and an endoscope apparatus 20 used along with the endoscope treatment tool 1 are combined together. FIG. 2 is an enlarged view showing a part of the endoscope apparatus 20 in an enlarged manner.

As shown in FIG. 1, the endoscope treatment tool 1 is a device used along with the endoscope apparatus 20 inserted into the inside of a body. As the endoscope apparatus 20, an endoscope apparatus having a well-known configuration can be appropriately selected and adopted. As shown in FIGS. 1 and 2, in the present embodiment, the endoscope apparatus 20 is illustrated having a tubular insertion body 21 inserted into the inside of the body, a side-view-type imaging unit 22 which is provided at a distal end of the insertion body 21, a tubular treatment tool channel 23 which allows the endoscope treatment tool 1 provided inside the insertion body 21 to be inserted therethrough, and a forceps elevator 24 which guides the endoscope treatment tool 1 inserted into the treatment tool channel 23, in the radial direction of the insertion body 21 at the distal end of the insertion body 21. As shown in FIG. 2, the endoscope apparatus 20 has the treatment tool channel 23 on the right of the imaging unit 22.

Figure 3:
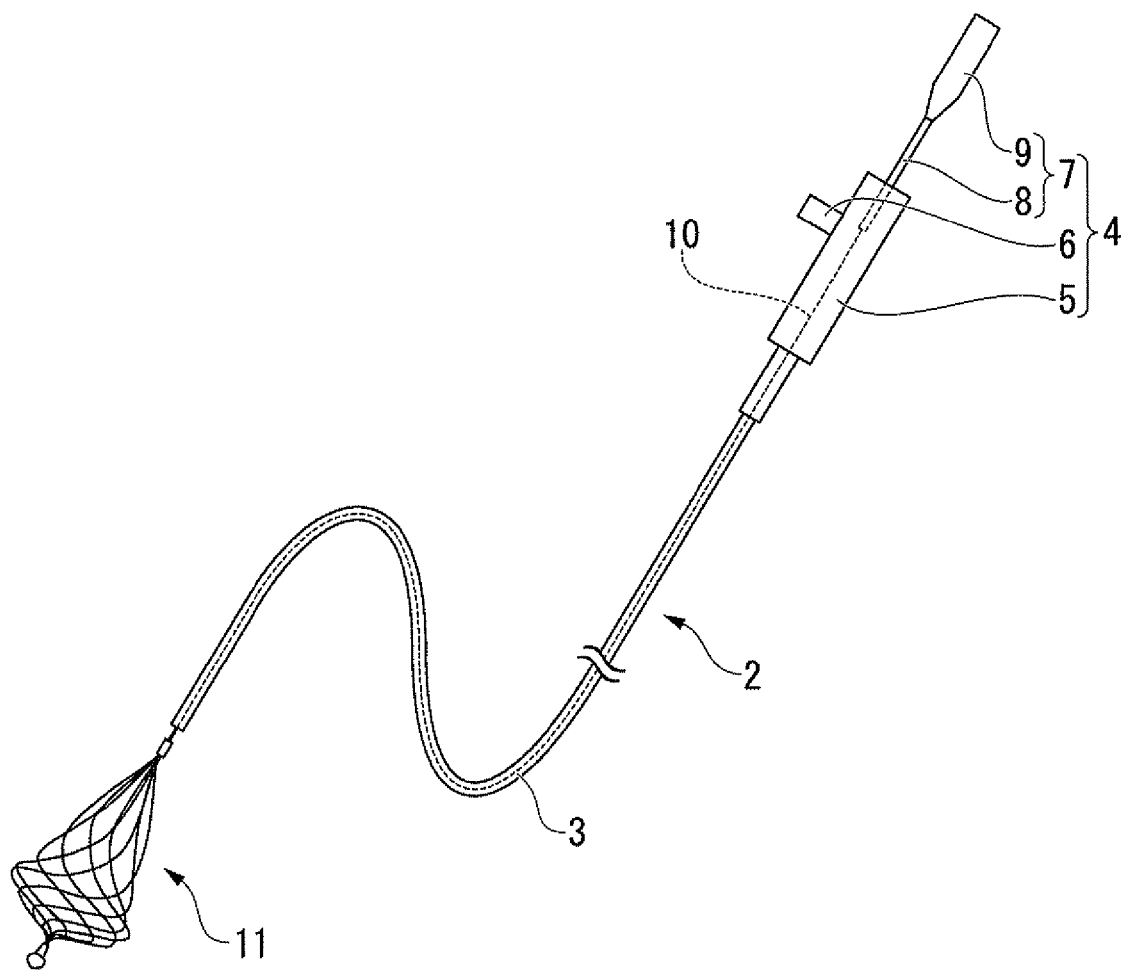
FIG. 3 is an overall view showing the endoscope treatment tool according to the first embodiment of the present invention.

FIG. 3 is an overall view showing the endoscope treatment tool 1.

As shown in FIG. 3, the endoscope treatment tool 1 includes a long insertion portion 2, and a manipulation wire 10 and a treatment portion 11 which are provided inside the insertion portion 2. The endoscope treatment tool 1 may include a manipulation portion 4 which is provided at one end of the insertion portion 2. In addition, the following description is made with the side where the manipulation portion 4 is provided in the length direction of the endoscope treatment tool 1 as the proximal side, and the opposite side of the side where the manipulation portion 4 is provided as the distal side.

The insertion portion 2 has a pliable flexible sheath 3 having an outside diameter capable of being inserted through the treatment tool channel 23 of the endoscope apparatus 20. As the materials of the flexible sheath 3, well-known resin materials, such as fluororesin and thermoplastic elastomer, a coil sheath formed by winding a metal wire rod, a blade using a metal wire, and the like can be appropriately selected, or these materials can be used in combination.

The manipulation portion 4 has a manipulation main body 5 fixed to the proximal end of the insertion portion 2, and a slider 7 slidingly movable with respect to the manipulation main body 5 in the direction of the central axis of the insertion portion 2.

The manipulation main body 5 is formed with a fluid supply port 6 which communicates with the inside of the flexible sheath 3. The fluid supply port 6 has, for example, a connecting means, such as a Luer lock structure, and a well-known syringe or a well-known pump can be connected to the fluid supply port 6.

The slider 7 has a shaft 8 of which the distal end is fixed to the proximal end of the manipulation wire 10, and a grip 9 which is fixed to the proximal end of the shaft 8.

Figure 4:
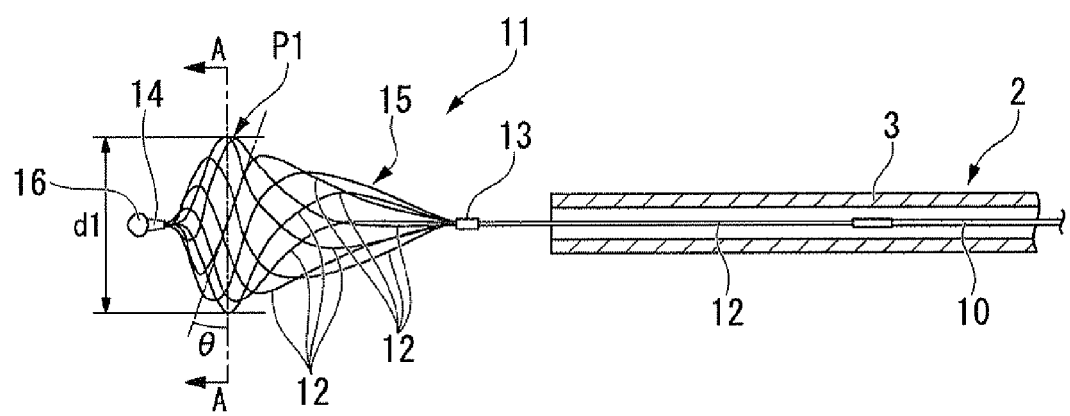
FIG. 4 is a partial cross-sectional view of the endoscope treatment tool according to the first embodiment of the present invention shown in a section along the central axis of an insertion portion of the endoscope treatment tool.
Figure 5:
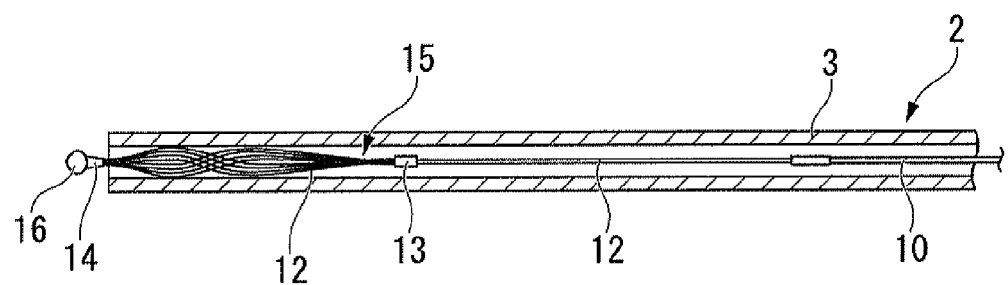
FIG. 5 is a partial cross-sectional view showing a state where a treatment portion is retracted into a flexible sheath in the same section as FIG. 4.
Figure 6:
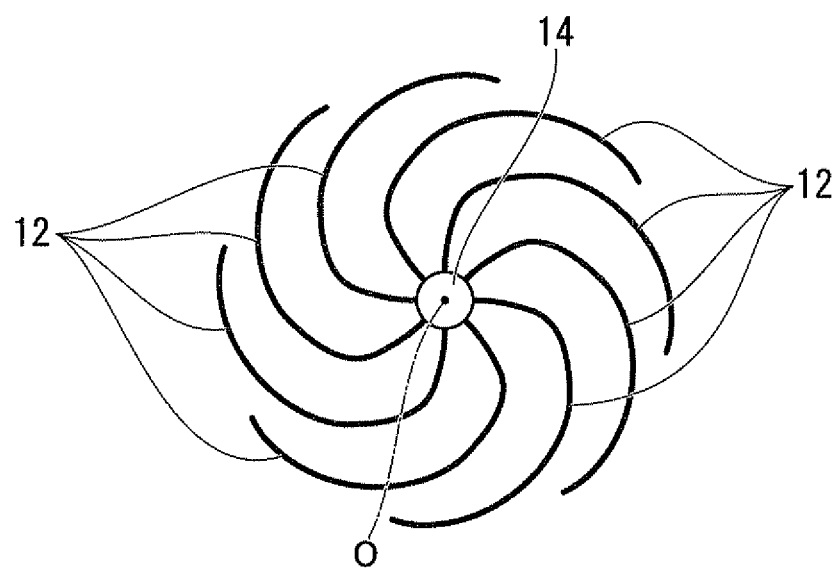
FIG. 6 is a cross-sectional view taken along a line A-A of FIG. 4.

FIG. 4 is a partial cross-sectional view of the endoscope treatment tool 1 shown in a section along the central axis of the insertion portion 2. FIG. 5 is a partial cross-sectional view showing a state where the treatment portion 11 is retracted into the flexible sheath 3 in the same section as FIG. 4. FIG. 6 is a cross-sectional view taken along a line A-A of FIG. 4.

As shown in FIGS. 3 and 4, the manipulation wire 10 is a wire of which the proximal end is arranged inside the manipulation main body 5 and the distal end is located in the vicinity of the distal end of the flexible sheath 3. The manipulation wire 10 advances and retracts within the flexible sheath 3 by the manipulation of the slider 7 of the manipulation portion 4. In the endoscope treatment tool 1, a stranded wire formed from a plurality of metal wire rods is adopted as the manipulation wire 10. Additionally, the manipulation wire 10 may adopt one or a plurality of single wires or stranded wires in order to easily transmit a projecting manipulation on the proximal side to the distal side. Moreover, the rigidity of the flexible sheath 3 itself is changed according to the length of the manipulation wire 10. Therefore, it is preferable to set the length as needed, such as lengthening the manipulation wire 10 in a case where it is desired that the pushability of the flexible sheath 3 be increased, or shortening the manipulation wire 10 in a case where it is desired that the manipulation wire be more easily inserted through the flexible sheath 3 with respect to bending of the endoscope insertion portion.

The treatment portion 11 is provided in order to capture foreign matter T (refer to FIG. 8), such as a calculus, in a body and to discharge the foreign matter T to the outside of the body. The treatment portion 11 has a plurality of elastic wires 12 which is fixed to the distal end of the manipulation wire 10, a first locking portion 13 which integrates the plurality of elastic wires 12 in parts of intermediate portions of the elastic wires 12, and a second locking portion 14 (a locking portion) which integrates the plurality of elastic wires 12 at the distal ends of the elastic wires 12. Additionally, in order to set the length of the manipulation wire 10 as needed as described above, the manipulation wire 10 may be extended to the first locking portion 13.

Additionally, in the endoscope treatment tool 1, the basket portion 15 is constituted by the elastic wires 12 located between the first locking portion 13 and the second locking portion 14.

As shown in FIGS. 4 and 6, the plurality of elastic wires 12 is made of a material having high elasticity, such as a superelastic alloy of a single wire or a stranded wire. As shown in FIG. 6, the plurality of elastic wires 12 in the basket portion 15 are formed in a helical shape in which the respective elastic wires are wound in the same direction over their entire length. Here, in a case where the expense is great if the helical shape is provided over the overall length of the elastic wires when the shape of the elastic wires 12 is formed, parts of the elastic wires may be formed into straight lines. In addition, in a case where parts of the elastic wires are formed into straight lines, it is desirable to provide straight portions on the proximal side of the elastic wires rather than the distal side where it is necessary to make the gaps in the elastic wires 12 dense so that a snared foreign matter is not easily lost.

In the endoscope treatment tool 1, in the basket portion 15, the plurality of elastic wires 12 is wound counterclockwise, as seen from the distal end of the manipulation wire 10 toward the second locking portion 14. As the materials of the elastic wires 12, for example, a nickel titanium alloy can be adopted. In addition, stainless steel, a stainless alloy, or the like may be adopted as the elastic wires 12. In the endoscope treatment tool 1, the basket portion 15 is constituted by eight elastic wires 12. However, the basket portion 15 only has to be constituted by a plurality of elastic wires 12 in consideration of the ease of snaring or the difficulty of losing a calculus.

Moreover, each of the plurality of elastic wires 12 is arranged at equal intervals around a centerline O, with a straight line which connects the proximal end and distal end of the basket portion 15 as the centerline O. Additionally, the position of the centerline O in the basket portion 15 substantially coincides with the position of an extended line obtained by extending the central axis of the manipulation wire 10 to the distal side.

The first locking portion 13 and the second locking portion 14 are desirably tubular members through which the plurality of elastic wires 12 is inserted, and are fixed to the plurality of elastic wires 12 by brazing, welding, swaging, resin welding, adhesives, and combinations of these. Additionally, the first locking portion 13 and the second locking portion 14 are not limited to the tubular members, and may be fixed to the elastic wires directly. The plurality of elastic wires 12 is held by the first locking portion 13 and the second locking portion 14 so as to spread in the shape of a cage in a state where an external force is not applied. The gap between the elastic wires 12 which spread in the shape of a cage is a gap for snaring foreign matter T which is a target to be treated, such as a calculus, inside the basket portion 15. Additionally, even if the gap in the initial state of the basket portion 15 is small, the elastic wires 12 are deformed when a calculus is snared, and a gap through which the foreign matter T enters is generated, so that the calculus can be snared.

A protective member 16 in a spherical shape or in a non-edged shape is attached to the distal end of the second locking portion 14 for the purpose of preventing the second locking portion 14 or the elastic wires 12 from being stuck or caught in a living body tissue. Additionally, the protective member 16 and the second locking portion 14 may be made of an integral member.

By advancing and retracting the manipulation wire 10 in the direction of the central axis of the flexible sheath 3, the basket portion 15 projects from the distal end of the flexible sheath 3, or retracts into the flexible sheath 3.

As shown in FIG. 4, when the basket portion 15 projects from the flexible sheath 3, the basket portion 15 becomes cage-shaped due to the restoring force of the elastic wires 12.

Additionally, as shown in FIG. 5, when the basket portion 15 retracts into the flexible sheath 3 from the opening at the distal end of the flexible sheath 3, the elastic wires 12 of the basket portion 15 are pushed by the inner surface of the flexible sheath 3. Thereby, the elastic wires 12 are elastically deformed such that the basket portion 15 becomes smaller than the inside diameter of the flexible sheath 3.

In this way, as the manipulation wire 10 is advanced and retracted in the direction of the central axis of the insertion portion 2, the basket portion 15 opens and closes in the radial direction orthogonal to the central axis of the manipulation wire 10.

As shown in FIG. 4, in a state where an external force is not applied to the basket portion 15, the diameter of the basket portion 15 becomes the maximum at a position closer to the second locking portion 14 than the intermediate position between the first locking portion 13 and the second locking portion 14. Hereinafter, the portion where the diameter of the basket portion 15 becomes the maximum is referred to as a maximum diameter portion P1 (a maximum outside diameter portion).

In the endoscope treatment tool 1, the outside diameter d1 of the maximum diameter portion P1 is set to a diameter such that each of the plurality of elastic wires 12 abuts a duct wall of a bile duct BD (refer to FIG. 8) on the circumference of the duct wall. Additionally, for the purpose of treating a case having a dilated portion in the bile duct BD, the outside diameter may be set to a diameter such that each of the plurality of elastic wires 12 abuts the duct wall of the dilated portion of the bile duct BD on the circumference of the duct wall of the dilated portion, based on the dilation diameter of the bile duct BD. In addition, in a case where the endoscope treatment tool 1 is used for luminal tissues other than the bile duct BD, the outside diameter d1 of the maximum diameter portion P1 is appropriately set based on the inside diameter of a targeted luminal tissue.

As shown in FIG. 4, each of elastic wires 12 of the basket portion 15 is formed in the shape of a helix of which the winding pitch becomes gradually smaller in a direction from the proximal end to the distal end of the manipulation wire 10. In the endoscope treatment tool 1, each of elastic wires 12 is wound within a range of about 225° in the circumferential direction from the first locking portion 13 to the second locking portion 14. Additionally, the angle at which the elastic wire 12 is wound in the circumferential direction is appropriately set according to the inclination of the elastic wire 12.

Moreover, in a state where an external force is not applied to the basket portion 15, the tangential line of each of the plurality of elastic wires 12 in the maximum diameter portion P1 is inclined at such an angle that the angle θ formed with respect to a plane orthogonal to the centerline O in the maximum diameter portion P1 becomes 45° or less. The elastic wires 12 have such a shape that the elastic wires 12 are directed to the axial direction on the proximal side thereof, are inclined laterally with respect to the plane orthogonal to the centerline O as they approach the maximum diameter portion P1, and are wound in the circumferential direction on the distal side thereof. In addition, the elastic wires 12 are formed three-dimensionally in a complicated shape, and have inflection points as shown in a projection view.

Figure 7:
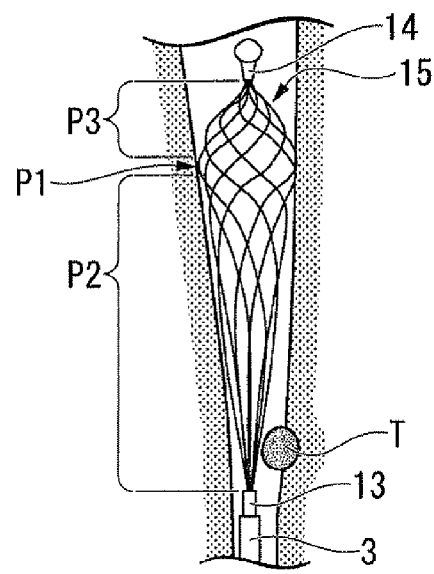
FIG. 7 is an explanatory view showing the operation of a basket portion in a luminal tissue.

Next, the principle of operation of the basket portion 15 in the endoscope treatment tool 1 is described. FIG. 7 is an explanatory view showing the operation of the basket portion 15 within a luminal tissue.

As shown in FIG. 7, the basket portion 15 is guided into, for example a luminal tissue, such as the bile duct BD, by the flexible sheath 3, and projects from the inside of the flexible sheath 3. When the basket portion 15 projects from the flexible sheath 3, the basket portion 15 is restored to a cage shape inside the luminal tissue by the restoring force of the elastic wires 12. Each of the elastic wires 12 in the basket portion 15 having a cage shape touches the inner surface of the luminal tissue, and is brought into close contact with the luminal tissue by being elastically deformed as each of the elastic wires 12 is pushed back by the luminal tissue.

In the endoscope treatment tool 1, the maximum diameter portion P1 of the basket portion 15 is pushed against the inner surface of the luminal tissue, and the portion of the basket portion 15 closer to the proximal side than the maximum diameter portion P1 becomes a snaring portion P2 for snaring foreign matter T, such as a calculus. Additionally, the portion of the basket portion 15 closer to the distal side than the maximum diameter portion P1 is configured such that the winding pitch of the elastic wires 12 is small and the gap between the elastic wires 12 is small, and becomes a capturing portion P3 from which the calculus snared in the basket portion 15 is not easily lost. Additionally, as the elastic wires 12 are brought into close contact with a bile duct before and behind the maximum diameter portion P1 or in a wide range, depending on the shape of the bile duct, and touch the duct wall of the bile duct in wider portion, foreign matter, such as a mud-like calculus which sticks to the duct wall of the bile duct, is more easily snared.

Figure 8:
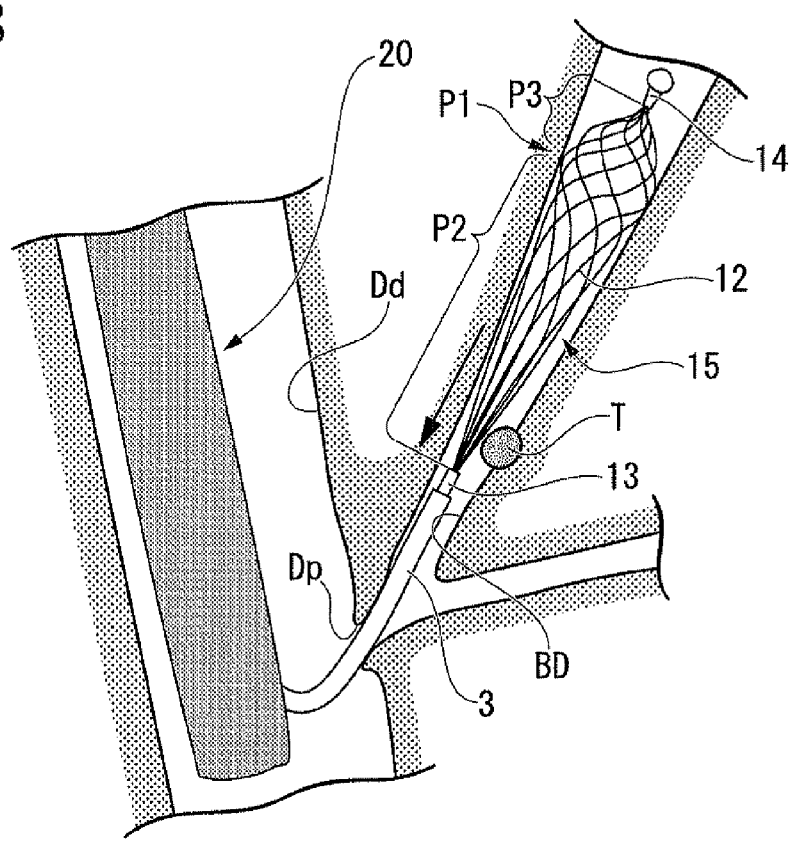
FIG. 8 is an explanatory view showing the operation of the basket portion in a bile duct.

Next, the operation of the basket portion 15 in a case where foreign matter T, such as a calculus generated inside the bile duct BD, is removed is described. FIG. 8 is an explanatory view showing the operation of the basket portion 15 in the bile duct BD.

As shown in FIG. 8, when the basket portion 15 is used for the purpose of removing, for example, a calculus inside the bile duct BD, the basket portion 15 is restored to a cage shape on the distal side of the foreign matter T inside the bile duct BD. Thereafter, the cage-shaped basket portion 15 is moved toward a duodenal papilla Dp, and snares the foreign matter T inside the bile duct BD in the basket portion 15. The foreign matter T snared in the basket portion 15 moves toward the duodenal papilla Dp while being snared in the elastic wires 12.

When the basket portion 15 moves toward the duodenal papilla Dp, the basket portion 15 enters the duodenal papilla Dp from the proximal end of the basket portion 15, each of the elastic wires 12 is pushed by the duodenal papilla Dp, and the proximal end of the basket portion 15 is reduced.

Figure 9:
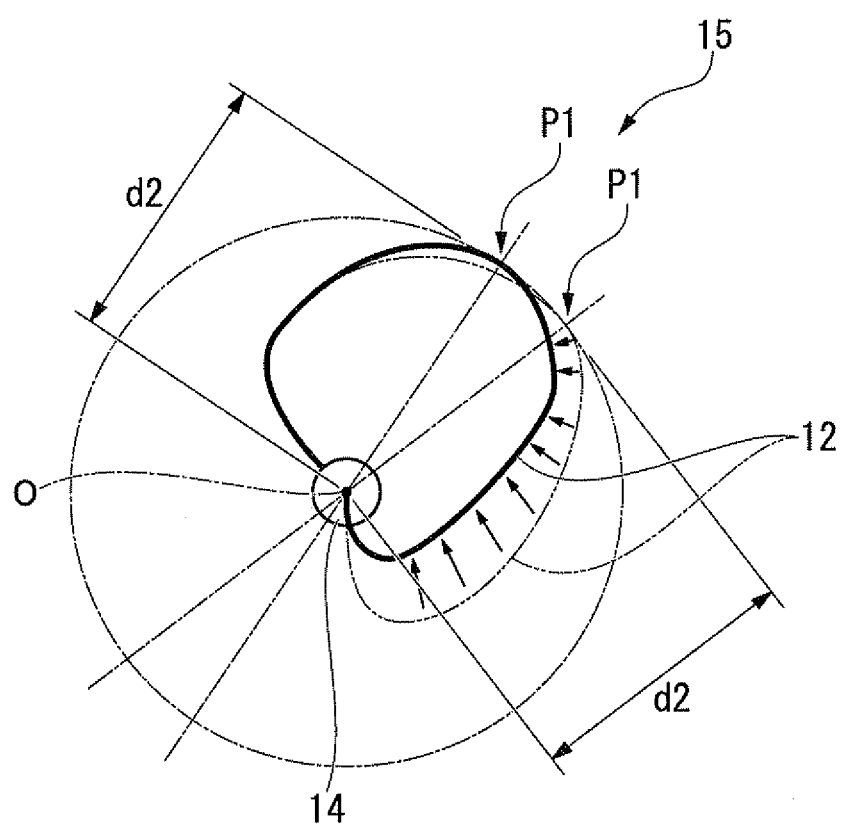
FIG. 9 is a view showing only one of a plurality of elastic wires which constitutes the basket portion and showing the operation of the elastic wire.
Figure 10:
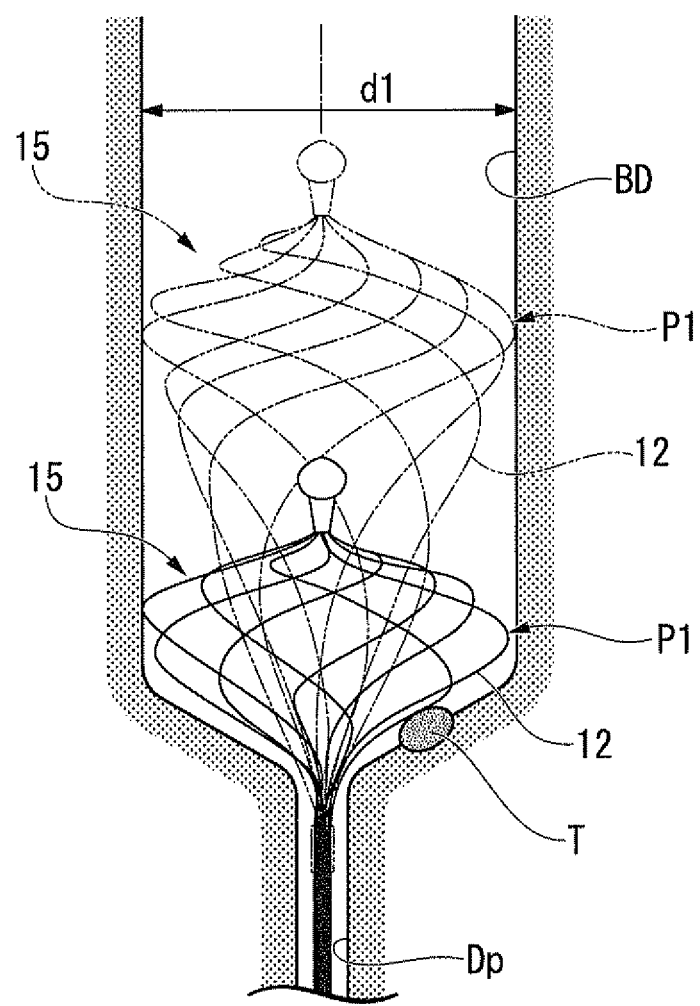
FIG. 10 is a view for describing a change in an outside dimension of a maximum diameter portion when the proximal side of the basket portion has been reduced.
Figure 11:
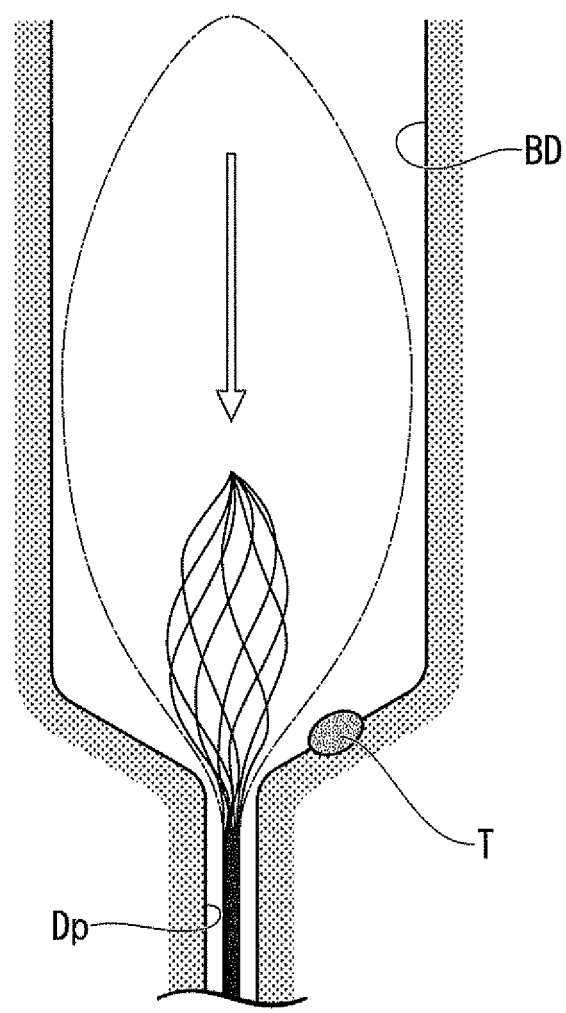
FIG. 11 is a view showing the operation of a prior-art basket.

FIG. 9 is a view showing only one of the plurality of elastic wires 12 which constitutes the basket portion 15 of FIG. 4 and showing the operation of the elastic wire 12. FIG. 10 is a view for describing a change in the outside diameter of the maximum diameter portion P1 when the proximal side of the basket portion 15 has been reduced.

As shown in FIGS. 4, 9, and 10, the winding pitch of the elastic wires 12 of the basket portion 15 becomes gradually small moving toward the second locking portion 14 from the first locking portion 13. For this reason, the elastic wire 12 located at the maximum diameter portion P1 of the basket portion 15 is pushed radially outward from the maximum diameter portion P1, by the force with which the elastic wire 12 at the proximal end of the basket portion 15 is pushed.

Additionally, in the endoscope treatment tool 1, the tangential line of the elastic wire 12 in the maximum diameter portion P1 is inclined at an angle which becomes 45° or less with respect to the plane orthogonal to the centerline O in the maximum diameter portion P1. Thus, the amount by which the basket portion 15 is reduced radially inward, and the amount by which the maximum diameter portion P1 is pushed radially outward are made substantially equal to each other. For this reason, even if the proximal side of the basket portion 15 is reduced, similarly to before the proximal side of the basket portion 15 is reduced, the position separated by a distance d2 from the centerline O becomes the maximum diameter portion P1. As a result, as shown in FIG. 10, in the process in which the proximal end of the basket portion 15 is retracted into the duodenal papilla Dp, the outside diameter of the maximum diameter portion P1 is maintained at substantially the same size as the outside diameter d1 of the maximum diameter portion P1 before the proximal end of the basket portion 15 is retracted into the duodenal papilla Dp. Thereby, the maximum diameter portion P1 of the basket portion 15 is brought into close contact with the inner wall of a lumen from the inside of the bile duct BD to the duodenal papilla Dp, so that foreign matter T, such as a calculus, can be snared in the basket portion 15 even in the vicinity of the duodenal papilla Dp.

Additionally, in a case where foreign matter T, such as a calculus, has entered the dilated portion of the bile duct BD in a case in which the bile duct BD in the vicinity of the duodenal papilla Dp is dilated, the difference in inside diameter between the bile duct BD in the vicinity of the duodenal papilla Dp, and the duodenal papilla Dp is greater than usual. Thus, a step generated at the boundary between the bile duct BD in the vicinity of the duodenal papilla Dp, and the duodenal papilla Dp is greater than usual. The stepped portion generated at the boundary between the bile duct BD in the vicinity of the duodenal papilla Dp, and the duodenal papilla Dp is generally a portion where the elastic wires of the basket do not reach easily. This is because the prior-art basket retracted into the duodenal papilla Dp is deformed so as to be reduced in whole (refer to FIG. 11).

As shown in FIG. 10, in the endoscope treatment tool 1, when the basket portion 15 is retracted into the duodenal papilla Dp from the proximal side of the basket portion 15, the maximum diameter portion P1 of the basket portion 15 reaches the boundary between the bile duct BD and the duodenal papilla Dp in a state where the outside diameter d1 of the maximum diameter portion P1 of the basket portion 15 is substantially maintained. For this reason, the maximum diameter portion P1 of the basket portion 15 reaches the step generated at the boundary between the bile duct BD and the duodenal papilla Dp. Thereby, foreign matter T which has entered the boundary between the bile duct BD and the duodenal papilla Dp is snared in the basket portion 15, and is captured by the capturing portion P3. By pulling out the basket portion 15 from the duodenal papilla Dp to the duodenum Dd, the foreign matter T snared in the basket portion 15 is removed out of the bile duct BD. In addition, since the maximum diameter portion P1 is located on a side of the second locking portion 14, even if the proximal side of the basket portion 15 is reduced, the maximum diameter portion P1 is maintained, and since the capturing portion P3 is close to the maximum diameter portion P1, the foreign matter T snared in the basket is not easily lost. Additionally, the bending angle of the elastic wires 12 bent from the second locking portion 14 is desirably 60° or more. As the bending angle is closer to 90°, the expansive force to the circumferential direction is maintained, and the basket portion 15 easily reaches the step between the bile duct BD and the duodenal papilla Dp. However, since an operating force required for opening/closing the basket becomes large if the angle of the elastic wires 12 approaches 90°, the bending angle is appropriately set. Moreover, when the elastic wires 12 are bent at a position very close to the second locking portion 14, the bending load is applied to the elastic wires, and the bending wires become easy to break, or the operating force required for opening/closing the basket becomes large. Therefore, the portions of the elastic wires 12 fixed to the second locking portion 14 desirably have a smooth round shape, have a plurality of bending portions, have a straight line portion, or the like.

Additionally, since the elastic wires 12 are inclined such that the angle θ of the elastic wires 12 in the maximum diameter portion P1 is 45° or less, the elastic wires 12 abut easily on the step generated at the boundary between the bile duct BD and the duodenal papilla Dp in the circumferential direction, and foreign matter T is more easily snared. On the other hand, in the prior-art basket, the angle θ is great and the elastic wires 12 are not inclined even if the elastic wires 12 have reached the step in a case where the step is small. Therefore, the elastic wires 12 abut the step in the axial direction, and foreign matter T is not easily snared.

Additionally, the outside diameter of the maximum diameter portion P1 while being pulled becomes greater than that of the maximum diameter portion P1 before being pulled due to the winding pitch of the elastic wires of the basket portion 15, the angle of the elastic wires in the maximum diameter portion P1, and the angle of the elastic wires wound in the circumferential direction, and thus, the elastic wires more easily reach the dilated bile duct.

Figure 12:
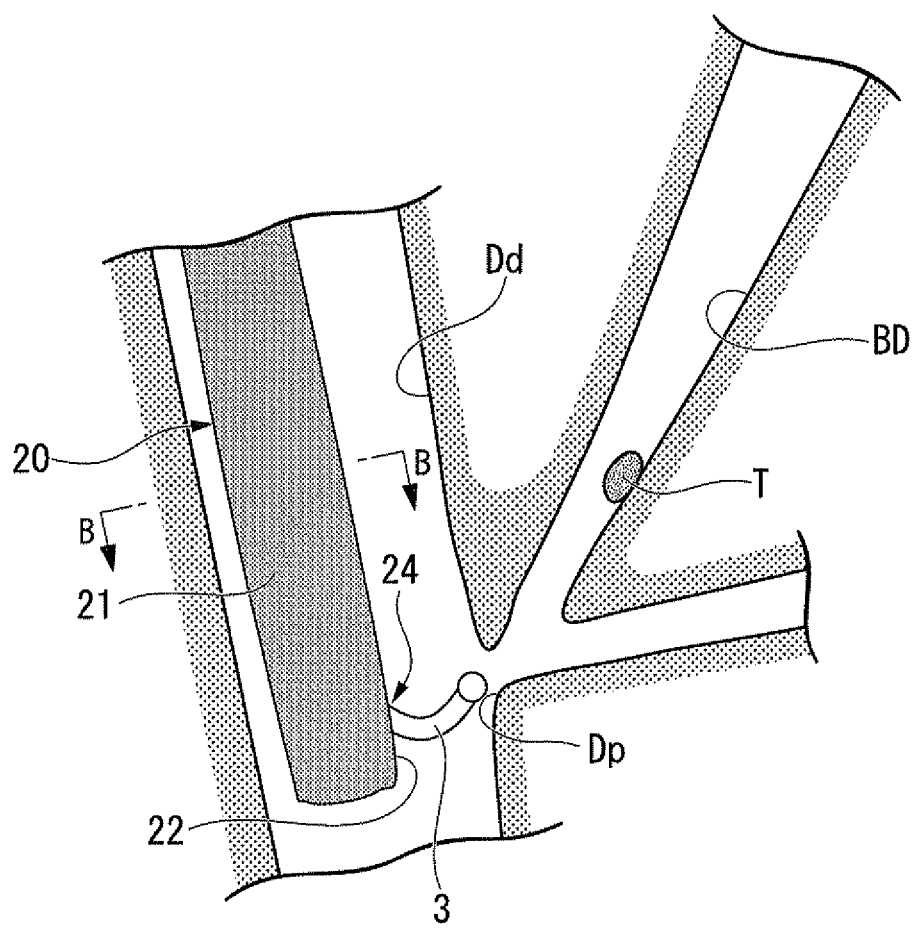
FIG. 12 is a view showing one process when the endoscope treatment tool according to the first embodiment of the present invention is used.
Figure 13:
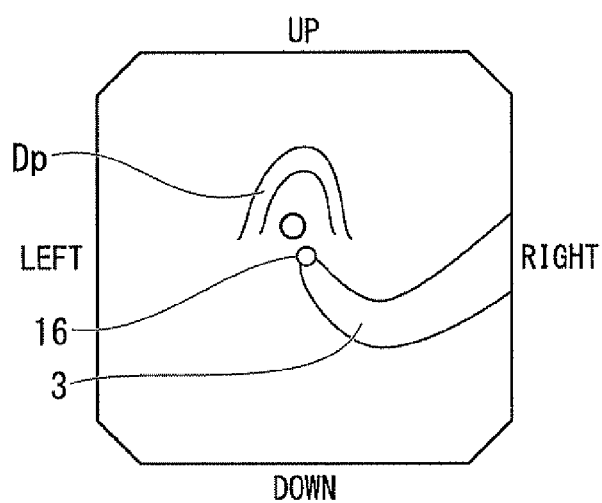
FIG. 13 is a view showing an example of an image picked up by an imaging unit of the endoscope apparatus.
Figure 14:
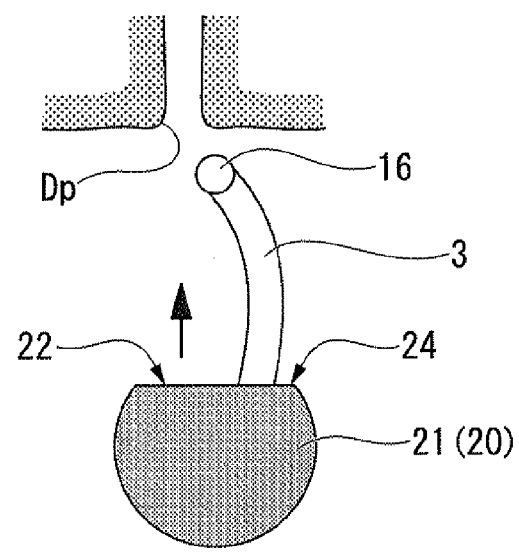
FIG. 14 is a cross-sectional view taken along a line B-B of FIG. 12.

Next, the flow of a procedure using the endoscope treatment tool 1 having the above-described configuration in combination with the endoscope apparatus 20 is shown, and the action of the endoscope treatment tool 1 is described. In the following, a procedure of removing foreign matter T, such as a calculus generated inside the bile duct BD in a case in which the bile duct BD is dilated, is described by way of an example. FIG. 12 is a view showing one process when the endoscope treatment tool 1 is used. FIG. 13 is a view showing an example of an image picked up by the imaging unit 22 of the endoscope apparatus 20. FIG. 14 is a cross-sectional view taken along a line B-B shown in FIG. 12.

The endoscope treatment tool 1 is prepared in a state where a treatment tool is received in the flexible sheath 3 (refer to FIG. 5).

First, as shown in FIG. 1, a user inserts the insertion body 21 of the endoscope apparatus 20 into the alimentary canal of a patient P via, for example, the mouth. Moreover, as shown in FIG. 12, the user guides the distal end of the insertion body 21 to the duodenum Dd, and locates the duodenal papilla Dp using the imaging unit 22.

As shown in FIG. 13, after the duodenal papilla Dp is caught within an imaging visual field of the imaging unit 22, the user makes the flexible sheath 3 project, the orientation of the insertion body 21 is changed in the radial direction by the forceps elevator 24, and the flexible sheath 3 is advanced into the imaging visual field from the right of the imaging visual field of the endoscope apparatus 20. Since the basket portion 15 in the treatment tool received in the flexible sheath 3 is formed in the shape of a helix in which the plurality of elastic wires 12 is wound counterclockwise as seen from the proximal side toward the distal side, as shown in FIGS. 13 and 14, the flexible sheath 3 is curved toward the left from the right of the imaging visual field.

For this reason, the distal end of the flexible sheath 3 is directed to the center of the imaging visual field, so that the distal end of the flexible sheath 3 can be easily caught within the imaging visual field. Additionally, the flexible sheath 3 is also curved along the helical shape of the basket portion 15, and a catheter naturally has a precurved shape. Since the user inserts the distal end of the flexible sheath 3 into the duodenal papilla Dp in this state, cannulation can be easily performed.

Figure 15:
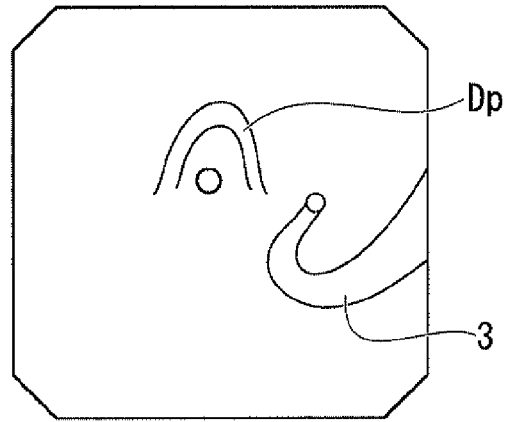
FIG. 15 is a view showing an example of an image picked up by the imaging unit of the endoscope apparatus.

In addition, when the plurality of elastic wires 12 is wound clockwise as seen from the proximal side toward the distal side, as shown in FIG. 15, the flexible sheath 3 bends to the right of the imaging visual field, and the distal end of the flexible sheath bends in a direction away from the papilla. Thus, cannulation cannot be easily performed.

The user inserts the flexible sheath 3 to a position beyond a calculus inside the bile duct BD, and makes the basket portion 15 project from the distal end of the flexible sheath 3 (refer to FIG. 8). This restores the basket portion 15 to a cage shape. The user pulls the basket portion 15 toward the duodenal papilla Dp and snares the calculus generated inside the bile duct BD in the basket portion 15 via the snaring portion P2 (refer to FIG. 10).

The user pulls out the basket portion 15 from the duodenal papilla Dp in a state where the foreign matter T, such as the calculus, is snared in the basket portion 15, and discharges the foreign matter T snared in the basket portion 15 into the duodenum Dd. The foreign matter T discharged into the duodenum Dd is then excreted. In addition, the user can also pull out the endoscope treatment tool 1 to the outside of the body along with the insertion body 21 of the endoscope apparatus 20 in a state where the foreign matter T, such as the calculus, is snared in the basket portion 15, and can take out the foreign matter T, such as the calculus, to the outside of the body.

In the prior art, in the process in which the basket is retracted into the duodenal papilla Dp from the bile duct BD, the basket is pushed in the direction in which the diameter of the basket becomes small by the inner surface of the duodenal papilla Dp, and the whole basket is reduced in size. For this reason, for example, in a case where the bile duct BD in the vicinity of the duodenal papilla Dp is dilated, there is a case where the basket does not reach foreign matter T which has entered the dilated portion of the bile duct BD.

On the other hand, according to the endoscope treatment tool 1 according to the present embodiment, even if the diameter of the proximal end of the basket portion 15 is reduced, the outside diameter of the maximum diameter portion P1 of the basket portion 15 is maintained. Thus, the maximum diameter portion P1 reaches the dilated portion in the vicinity of the papilla. For this reason, the calculus which has entered the dilated portion can be snared in the basket portion 15 in the maximum diameter portion P1 and before and behind the maximum diameter portion P1.

Additionally, since the winding pitch of the elastic wires 12 on the distal side of the basket portion 15 becomes smaller than that on the proximal side of the basket portion 15, a possibility that the calculus caught in the capturing portion P3 is lost from the gap between the elastic wires 12 can be suppressed. For this reason, a possibility that the calculus once snared by the basket portion 15 is lost can be reduced, and the calculus can be more reliably removed.

In addition, the endoscope treatment tool 1 according to the present embodiment is not limited to the above-described configuration, and design changes can be appropriately made.

For example, the basket portion 15 arranged in the flexible sheath 3 may be configured such that the plurality of elastic wires 12 is wound clockwise, as seen from the distal end of the manipulation wire 10 toward the second locking portion 14. In a case where the flexible sheath 3 is inserted into the treatment tool channel 23 on the left of the imaging visual field in the above-described endoscope apparatus 20, and is used, the basket portion 15 having such a configuration is curved such that the distal end of the flexible sheath 3 is directed to the center of the imaging visual field. For this reason, there is an effect that the flexible sheath 3 can be easily inserted into a part to be inserted in the usage in which the insertion portion 2 is inserted into the treatment tool channel 23 on the left of the imaging visual field. That is, it is preferable that the winding direction of the plurality of elastic wires 12 be set based on the positional relationship between the imaging unit 22 and the treatment tool channel 23.

Figure 16:
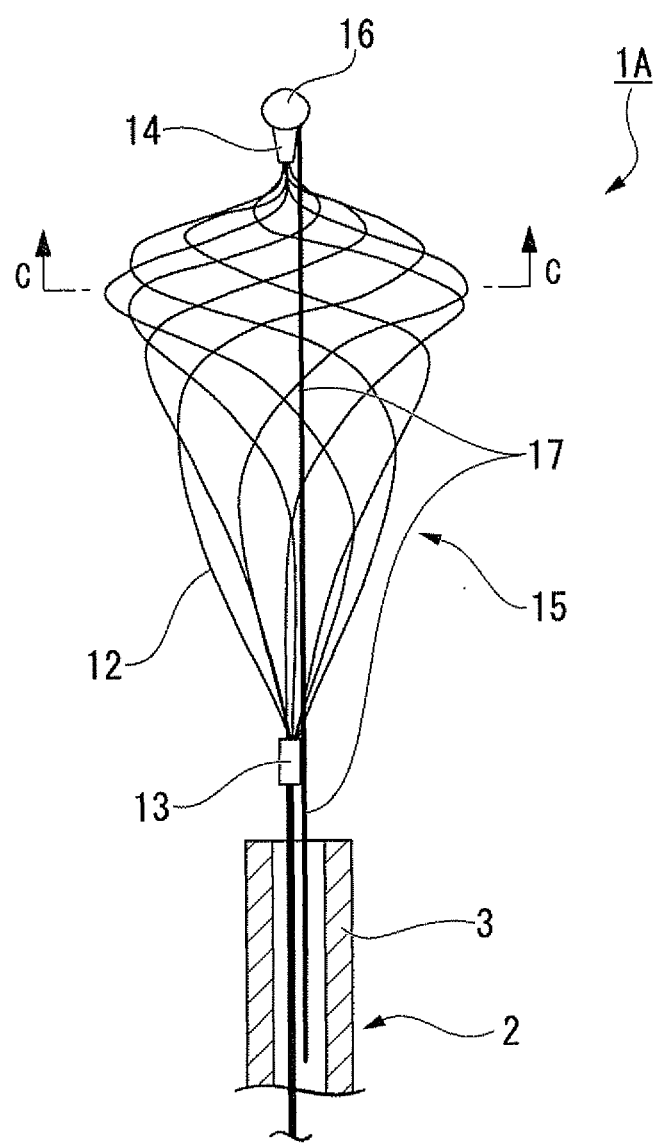
FIG. 16 is an enlarged view of a basket portion in an endoscope treatment tool according to a second embodiment of the present invention.
Figure 17:
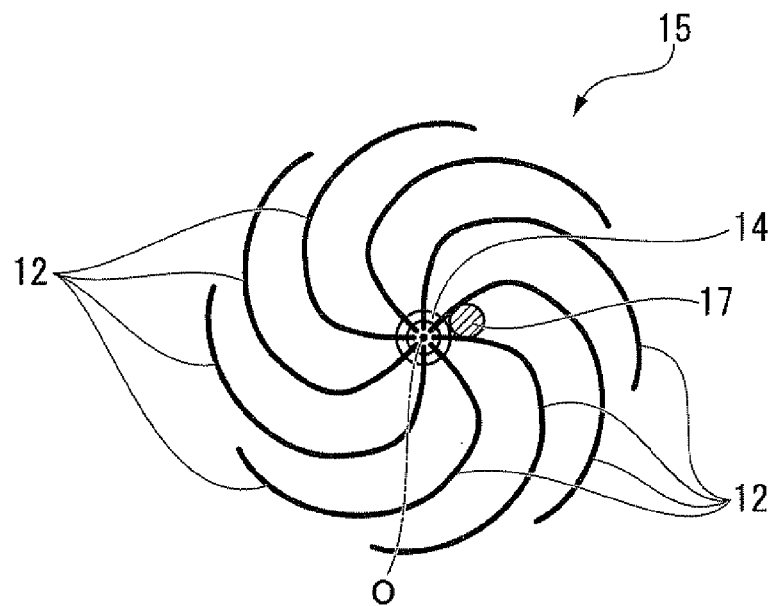
FIG. 17 is a cross-sectional view taken along a line C-C of FIG. 16.

Next, an endoscope treatment tool 1A according to a second embodiment of the present invention is described with reference to FIGS. 16 to 19. FIG. 16 is an enlarged view of a basket portion 15 in the endoscope treatment tool 1A. FIG. 17 is a cross-sectional view taken along a line C-C of FIG. 16.

Hereinafter, the same components as those of the endoscope treatment tool 1 described in the above-described first embodiment are designated by the same reference numerals and duplicate descriptions are omitted.

As shown in FIGS. 16 and 17, the endoscope treatment tool 1A is different from the endoscope treatment tool 1 in that the endoscope treatment tool 1A includes a support member 17 fixed to the second locking portion 14.

The support member 17 is a wire rod having elasticity, and has a distal end fixed to the outer peripheral surface of the second locking portion 14. The central axis of the support member 17 does not coincide with the central axis of the second locking portion 14, and becomes substantially parallel to the central axis of the second locking portion 14. That is, the support member 17 is arranged at a position shifted from the centerline (the centerline O of the basket portion 15) of the plurality of elastic wires 12 integrated by the second locking portion 14.

The proximal end of the support member 17 which is the side opposite to the side of the support member 17 which is fixed to the second locking portion 14 is inserted into the flexible sheath 3. The support member 17 is not fixed to the elastic wires 12 and the manipulation wire 10, and is configured to be able to advance and retract in the direction of the central axis of the flexible sheath 3 independently from the elastic wires 12 and the manipulation wire 10 inside the flexible sheath 3. Even in a state where the basket portion 15 projects as much as possible from the distal end of the flexible sheath 3, the length of the support member 17 is set to such a length that the proximal end of the support member 17 is located within the flexible sheath 3. Additionally, in order to avoid a situation where the proximal end surface of the support member 17 is caught in the flexible sheath 3 at the time of projection and retraction of the basket, the support member 17 may be arranged on the proximal side of an endoscope angle portion, or may be arranged up to the manipulation portion on the proximal side. In addition, in a case where the support member 17 is arranged up to the manipulation portion on the proximal side, the shape of the basket can be deformed by projecting and retracting the support member 17 by the manipulation on the proximal side, and a means for removing a calculus snared in the basket portion 15 from the inside of the basket can be obtained.

Figure 18:
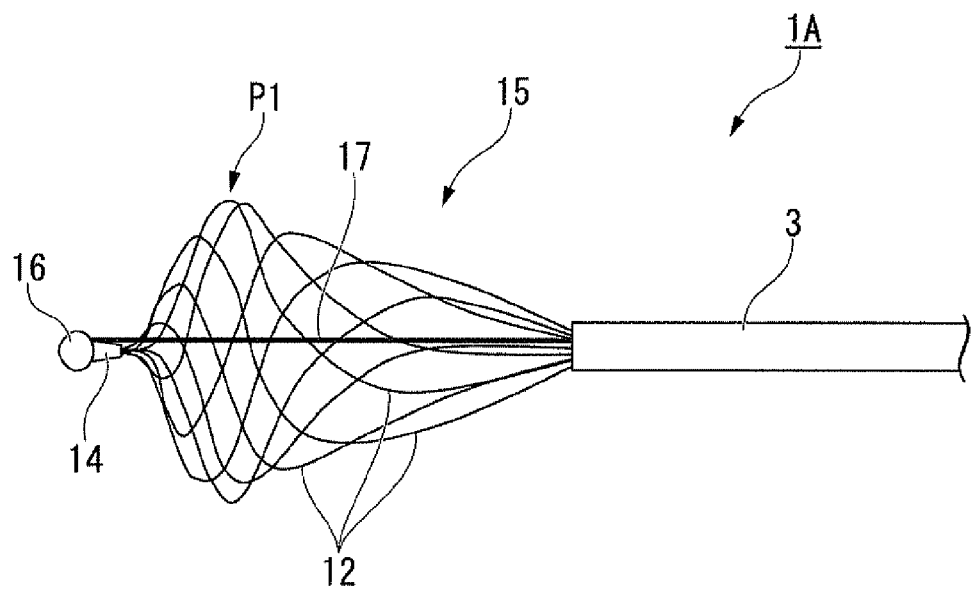
FIG. 18 is an explanatory view showing the action of the endoscope treatment tool according to the second embodiment of the present invention.
Figure 19:
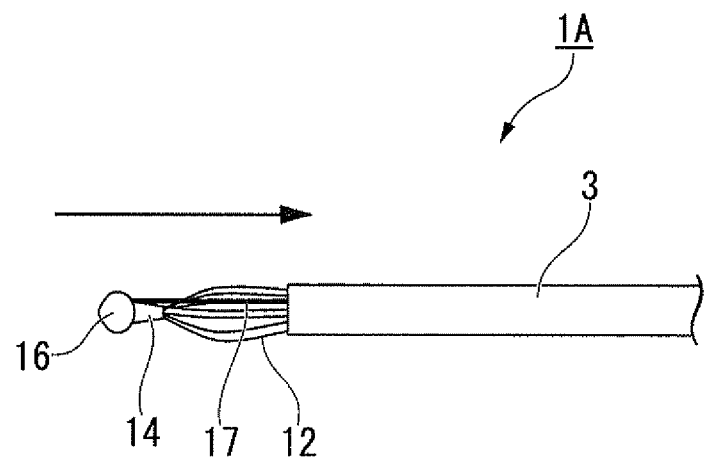
FIG. 19 is an explanatory view showing the action of the endoscope treatment tool according to the second embodiment of the present invention.
Figure 20:
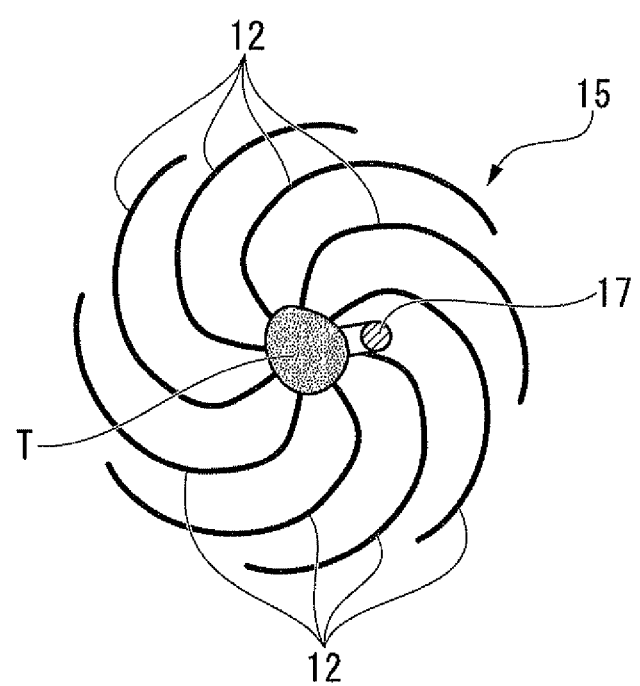
FIG. 20 is a view for describing the operation of the basket portion when the endoscope treatment tool according to the second embodiment of the present invention is used.

The action of the endoscope treatment tool 1A is described. FIGS. 18 and 19 are explanatory views showing the action of the endoscope treatment tool 1A. FIGS. 18 and 19 are views for describing the operation of the basket portion 15 when the endoscope treatment tool 1A is used. FIG. 20 is a view for describing the operation of the basket portion 15 when the endoscope treatment tool 1A is used, and is a cross-sectional view taken along the line C-C of FIG. 16 after foreign matter T is snared.

When the endoscope treatment tool 1A is used, the distal end of the flexible sheath 3 is inserted into the bile duct BD from the duodenal papilla Dp similarly to that described in the above-described first embodiment (refer to FIG. 8). After the distal end of the flexible sheath 3 is arranged inside the bile duct BD, the slider 7 shown in FIG. 1 is pushed to a side of the manipulation main body 5 by the manipulation of a user. Thereby, the basket portion 15 is pushed out from the distal end of the flexible sheath 3 by the manipulation wire 10 coupled to the slider 7. The basket portion 15 pushed out from the distal end of the flexible sheath 3 is restored to its original cage shape by the elasticity of the elastic wires 12.

Here, after the basket portion 15 is restored to a cage shape, for example, it may be necessary to adjust the position of the basket portion 15 in the bile duct BD. In this case, the basket portion 15 is retracted into the flexible sheath 3, and the distal end of the flexible sheath 3 is moved to a desired position. Thereafter, the basket portion 15 is projected from the distal end of the flexible sheath 3 again.

When the basket portion 15 is retracted into the flexible sheath 3, the slider 7 is pulled out from the manipulation main body 5 by the manipulation of the user (refer to FIG. 1). Then, as shown in FIGS. 18 and 19, the basket portion 15 begins to be retracted into the flexible sheath 3 by the manipulation wire 10 coupled to the slider 7.

At this time, the diameter of the proximal end of the basket portion 15 is reduced as the basket portion 15 is gradually retracted into the flexible sheath 3 from the proximal end side of the basket portion 15. Moreover, similarly to that described in the first embodiment, the outside diameter of the maximum diameter portion P1 of the basket portion 15 is maintained, or increases.

When the basket portion 15 is further retracted into the flexible sheath 3, the support member 17 is retracted in response to the movement of the distal end thereof. For this reason, the support member 17 functions as a core which supports the basket portion 15 substantially along the centerline O (refer to FIG. 17) of the basket portion 15. For this reason, the plurality of elastic wires 12 of the basket portion 15 is aligned in the shape of a helix in which the central axis of the support member 17 becomes substantially the center.

Thereafter, the elastic wires 12 of the basket portion 15 are retracted into the flexible sheath 3 while being aligned by the action of the support member 17. Thereby, the basket portion 15 is housed in the flexible sheath 3 in a straight line along the support member 17.

Subsequently, the user moves the distal end of the flexible sheath 3 to a desired position, and makes the basket portion 15 project again from the distal end of the flexible sheath 3, thereby restoring the basket portion 15 to a cage shape. Moreover, foreign matter T, such as a calculus, is snared in the basket portion 15 similarly to the endoscope treatment tool 1 according to the above-described first embodiment.

As shown in FIGS. 17 and 20, since the central axis of the support member 17 is arranged at a position shifted from the centerline O of the plurality of elastic wires 12 integrated by the second locking portion 14, the support member 17 is pushed away radially outward with respect to the centerline O by the foreign matter T, such as a calculus. Thereby, the foreign matter T, such as a calculus, is located on the centerline O of the basket portion 15. For this reason, in the capturing portion P3, the foreign matter T can be caught in a portion with a narrow gap between the elastic wires 12. In addition, in a state where the foreign matter T is held on the central axis of the second locking portion 14, the gaps in the plurality of elastic wires 12 which surround the foreign matter T are made substantially equal to each other. As a result, a possibility that the foreign matter T is lost from the basket portion 15 can be suppressed to be low as compared to a case where the central axis of the support member 17 is located on the centerline O of the basket portion 15.

Additionally, according to the endoscope treatment tool 1A, the elastic wires 12 are aligned and retracted into the flexible sheath 3. Thus, when the basket portion 15 is received into the flexible sheath 3, it is possible to suppress mutual crossing of the elastic wires 12. Thereby, in a case where the basket portion 15 is received into the flexible sheath 3, it is possible to suppress the elastic wires 12 from becoming entangled or the basket portion 15 becoming twisted or toppled. Additionally, cannulation may be more easily performed by bending the support member 17 to such a degree that the basket is not twisted or toppled, thereby forcing the flexible sheath 3 to be curved, and giving a precurved shape to the flexible sheath 3 to a greater extent than when only helical basket wires are used.

Figure 21:
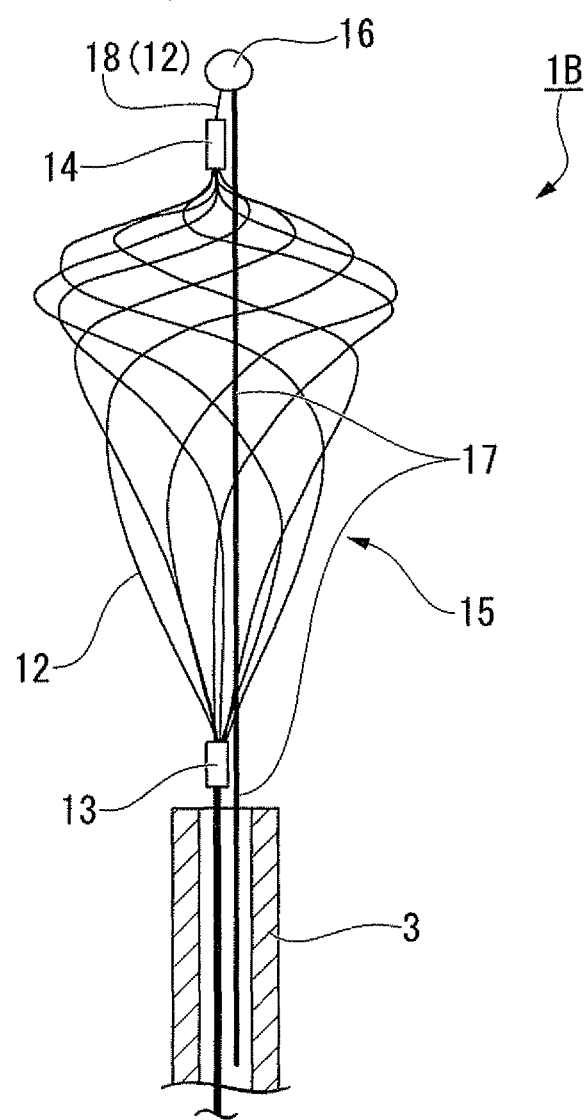
FIG. 21 is an enlarged view of a basket portion in an endoscope treatment tool according to a third embodiment of the present invention.

Next, an endoscope treatment tool 1B according to a third embodiment of the present invention is described with reference to FIGS. 21 to 25. FIG. 21 is an enlarged view of the basket portion 15 in the endoscope treatment tool 1B. FIGS. 22 to 25 are explanatory views for describing the action of the basket portion 15.

As shown in FIG. 21, in the endoscope treatment tool 1B, some of the elastic wires 12 of the basket portion 15 further extend toward the distal side from the second locking portion 14, and the support member 17 described in the second embodiment is fixed to the portions of the elastic wires 12 which extend toward the distal side from the second locking portion 14. In other respects, the configuration is the same as the configuration of the endoscope treatment tool 1A described in the above-described second embodiment.

In the endoscope treatment tool 1B, the portions of the plurality of elastic wires 12 which extend to the distal side from the second locking portion 14 become a coupling portion 18 for coupling with the support member 17. Additionally, the distal end of the support member 17 is fixed to the distal end of the coupling portion 18. As methods of fixing the support member 17 and the coupling portion 18, well-known methods, such as brazing, swaging, welding, adhesion, resin welding, and combinations thereof, are appropriately adopted. In this way, in the endoscope treatment tool 1B, the support member 17 is fixed to the second locking portion 14 via the coupling portion 18.

Additionally, for the purpose of preventing the support member 17 or the coupling portion 18 from being stuck in a living body tissue, a protective member 16 in a spherical shape or in a non-edged shape is provided at the distal ends of the support member 17 and the coupling portion 18 so as to cover the distal ends of the support member 17 and the coupling portion 18.

The action of the endoscope treatment tool 1B is described. FIGS. 22 to 25 are explanatory views for describing the action of the basket portion 15 of the endoscope treatment tool 1B.

Figure 22:
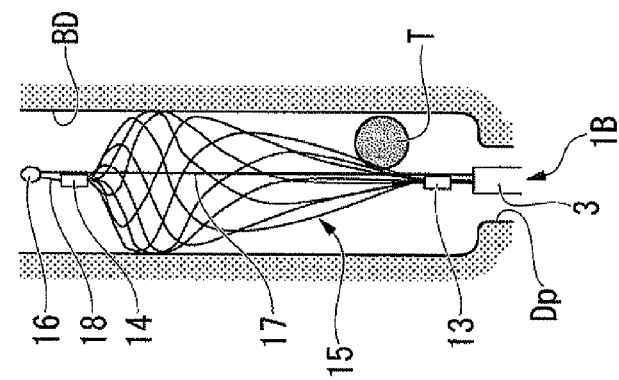
FIG. 22 is an explanatory view for describing the action of the basket portion in the endoscope treatment tool according to the third embodiment of the present invention.

When the endoscope treatment tool 1B is used, similarly to the endoscope treatment tool 1A according to the above-described second embodiment, the distal end of the flexible sheath 3 is inserted into the bile duct BD, and the basket portion 15 is pushed out from the distal end of the flexible sheath 3 (refer to FIG. 22).

Figure 23:
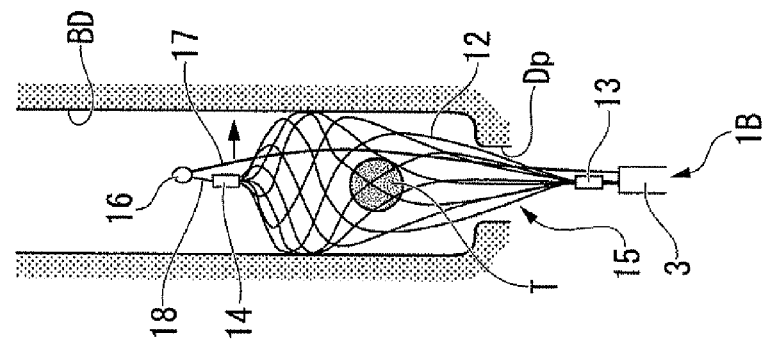
FIG. 23 is an explanatory view for describing the action of the basket portion in the endoscope treatment tool according to the third embodiment of the present invention.

As shown in FIG. 23, when the basket portion 15 is pulled toward the duodenal papilla Dp, foreign matter T, such as a calculus, is snared in the inside of the basket portion 15.

Figure 24:
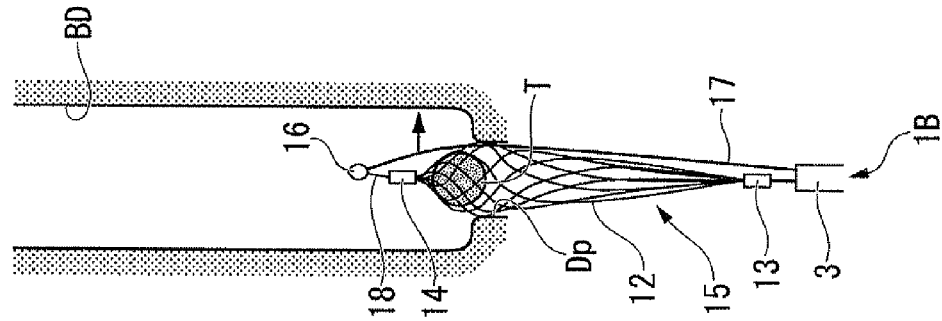
FIG. 24 is an explanatory view for describing the action of the basket portion in the endoscope treatment tool according to the third embodiment of the present invention.

As shown in FIG. 24, the basket portion 15 is gradually reduced from the proximal side as it is retracted into the duodenal papilla Dp. For this reason, the foreign matter T moves toward the distal end of the basket portion 15, and the support member 17 is pushed radially outward from the basket portion 15 by the foreign matter T. Since the coupling portion 18 is constituted by the elastic wires 12, as the elastic wires 12 are elastically deformed, the support member 17 moves radially outward from the basket portion 15. For this reason, at the proximal end of the second locking portion 14, gaps for holding foreign matter T on the central axis of the second locking portion 14 are generated. For this reason, it is possible to suppress widening of the gaps in some of the plurality of elastic wires 12, and it is possible to suppress the possibility that foreign matter T is lost to a low level.

Figure 25:
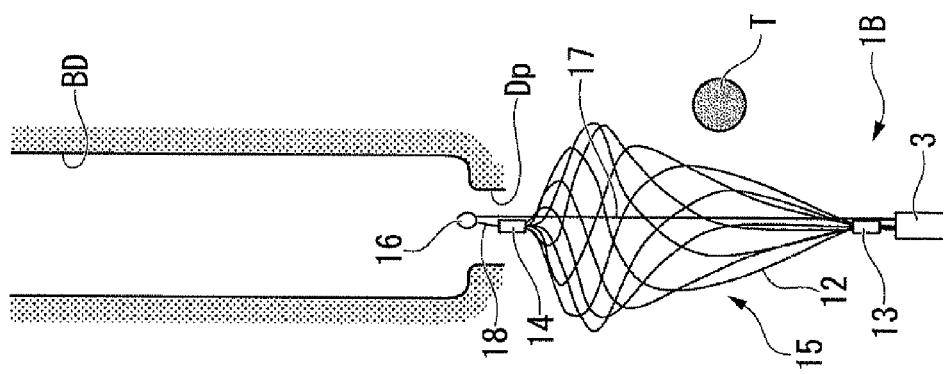
FIG. 25 is an explanatory view for describing the action of the basket portion in the endoscope treatment tool according to the third embodiment of the present invention.

As shown in FIG. 25, when the basket portion 15 is pulled out from the duodenal papilla Dp, the basket portion 15 is restored to a cage shape, and foreign matter T, such as a calculus, is discharged into the duodenum Dd.

According to the endoscope treatment tool 1B according to the present embodiment, the support member 17 is fixed to the coupling portion 18 constituted by the elastic wires 12. Thus, the movable range of the support member 17 can be made wider than that of the example described in the above-mentioned second embodiment. Thereby, the gaps for holding foreign matter T, such as a calculus, can be widely opened, and larger foreign matter T can be held in the basket portion 15.

Additionally, since the coupling portion 18 is constituted by some of the elastic wires 12 which constitute the basket portion 15, the second locking portion 14 can be made to have a smaller diameter than that of the case where another new member is attached in order to provide the coupling portion 18. Thereby, the coupling portion 18 can be included while an increase in the diameter of the basket portion 15 is suppressed.

Additionally, since the coupling portion 18 is composed of wires having elasticity, the support member 17 is restored to the position adjacent to the second locking portion 14 and the coupling portion 18 by the restoring force of the coupling portion 18 in a state where the support member 17 is not pushed by foreign matter T. Thereby, similarly to the endoscope treatment tool 1A according to the above-described second embodiment, when the basket portion 15 is received in the flexible sheath 3, the elastic wires 12 can be aligned. Additionally, the coupling portion 18 is not limited to the elastic wires 12, and may be another members which are more easily deflected than the elastic wires, or another members which are not easily deflected.

In addition, the endoscope treatment tool according to the above-described embodiments can be used in a case where foreign matter is removed from a papilla, as well as in a case where a calculus is mechanically broken up by a compressive force of the basket portion 15 and the flexible sheath 3 due to pulling the manipulation wire 10. In the latter case, the manipulation portion 4 is configured such that the manipulation wire 10 can be pulled by a sufficient force.

In the above-described embodiments, a bile duct has been given as an example of the luminal tissue which becomes a target into which the flexible sheath is inserted. According to the endoscope treatment tool according to the present invention, however, foreign matter can be removed in a case where the foreign matter is generated inside a lumen, such as a pancreatic duct, a ureter or a blood vessel, besides the bile duct.

While preferred embodiments of the present invention have been described, the present invention is not limited to the embodiments. Additions, omissions, substitutions, and other modifications can be made to the present invention without departing from the spirit and scope of the present invention. The present invention is not limited to the above-mentioned description, and is only limited by the scope of the appended claims.

What is claimed is:

1. An endoscope treatment tool comprising:
a flexible sheath;
a manipulation wire inserted through the flexible sheath so as to freely advance and retract; and
a basket portion which is connected at a proximal end of the basket portion to a distal side of the manipulation wire, the basket portion including a locking portion provided at a distal end of the basket portion, the basket portion including a plurality of elastic wires integrated by the locking portion, the basket portion opens and closes in a radial direction orthogonal to a central axis of the manipulation wire, wherein
the basket portion defines a longitudinal extent with a center, and a maximum outside diameter portion of the basket portion is at a position closer to the locking portion and the center of the longitudinal extent of the basket portion,
the plurality of elastic wires is formed in a shape of a helix in which each of the plurality of elastic wires is helically wound in a same direction over an entire length of the plurality of elastic wires, and a winding pitch of the plurality of elastic wires becomes gradually smaller in a direction from a proximal side of the manipulation wire to the distal side of the manipulation wire, and a gap between the plurality of elastic wires is smaller at a portion between the locking portion and the maximum outside diameter portion than at a portion between the proximal end of the basket portion and the maximum outside diameter portion, with the winding pitch at its smallest at the distal end of the basket portion, and
a tangential line of each of the plurality of elastic wires in the maximum outside diameter portion is inclined at an angle of 45° or less with respect to a plane orthogonal to the central axis without an external force applied to the basket portion, and thereby, when a proximal side of the basket portion is reduced, the maximum outside diameter portion is pushed outward in the radial direction by a first amount which is substantially the same as a second amount by which the proximal side of the basket portion is reduced inward in the radial direction, and an outside diameter of the maximum outside diameter portion is maintained at substantially a same size as the outside diameter before the proximal side of the basket portion is reduced.

2. The endoscope treatment tool according to claim 1, wherein the basket portion includes a support member coupled to the locking portion which is at least partially inserted into the flexible sheath.

3. The endoscope treatment tool according to claim 2, wherein the support member is arranged at a position shifted from a centerline of the plurality of elastic wires integrated by the locking portion.

4. The endoscope treatment tool according to claim 2, further comprising a coupling portion further extending to a distal side of the basket portion from the locking portion, wherein the support member is fixed to the coupling portion.

5. The endoscope treatment tool according to claim 1, wherein the elastic wires are made of a nickel titanium alloy.

6. The endoscope treatment tool according to claim 1, wherein the plurality of elastic wires is wound counterclockwise, as seen from a proximal end of the manipulation wire toward a distal end of the manipulation wire.

7. The endoscope treatment tool according to claim 1, wherein each of the plurality of the elastic wires is wound counterclockwise, when viewed from the distal side of the manipulation wire toward the locking portion.

8. The endoscope treatment tool according to claim 1, wherein each of the plurality of the elastic wires has two inflection points from the proximal end to the distal end of the basket portion.

* * * * *